United States Patent
Herrmann et al.

(10) Patent No.: US 6,316,946 B2
(45) Date of Patent: *Nov. 13, 2001

(54) MICROWAVE LEAKAGE FIELD SENSOR FOR MEASURING MOISTURE AND/OR DENSITY

(75) Inventors: Rainer Herrmann, Hamburg; Stefan Zaage, Hannover, both of (DE)

(73) Assignee: Manfred Tews, Hamburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/154,563

(22) Filed: Sep. 16, 1998

(30) Foreign Application Priority Data

Sep. 16, 1997 (DE) .......................... 297 16 639 U

(51) Int. Cl.[7] .............................. G01R 27/04; G01R 27/32
(52) U.S. Cl. .................................................... 324/632
(58) Field of Search ..................... 324/632, 634, 324/636, 643, 640; 73/29.01, 73; 333/227, 230, 231

(56) References Cited

U.S. PATENT DOCUMENTS

| 4,270,083 | * | 5/1981 | Fitzky et al. ................... 324/58.5 |
| 4,297,874 | * | 11/1981 | Sasaki ................................ 73/73 |
| 4,829,233 | * | 5/1989 | Flemming et al. ............... 324/58.5 |
| 4,890,054 | * | 12/1989 | Maeno et al. ................... 324/58.5 |
| 5,321,360 | * | 6/1994 | Mansfield ......................... 324/322 |
| 5,786,740 | * | 7/1998 | Ishikawa et al. ................ 333/219.1 |
| 5,826,458 | * | 10/1998 | Little ................................... 73/73 |

FOREIGN PATENT DOCUMENTS

| 2 166 873 A | 5/1986 | (GB) . |
| WO 91 12518 A | 8/1991 | (WO) . |

OTHER PUBLICATIONS

"Mesures Regulation Automatisme", Bd. 50, Nr. 1, Jan. 1985.

F. Thompson, "Moisture Measurement Using Microwaves", Measurement & Control Bd., 22, Nr., Sep. 1989.

European Search Report, Mar. 4, 1998.

* cited by examiner

*Primary Examiner*—Safet Metjahic
*Assistant Examiner*—E P LeRoux
(74) *Attorney, Agent, or Firm*—Alix, Yale & Ristas, LLP

(57) ABSTRACT

The microwave leakage field sensor for measuring moisture and/or density of dielectric materials is distinguished by the fact that it is of essentially rotationally symmetrical design and transmissive for electromagnetic radiation in the axial direction toward at least one side, and that an essentially rotationally symmetrical alternating field of standing waves can be generated in it, the spatial period of which field in the peripheral direction is less than the vacuum wavelength at the frequency of the alternating field.

17 Claims, 3 Drawing Sheets

MICROWAVE LEAKAGE FIELD SENSOR FOR MEASURING MOISTURE AND/OR DENSITY

BACKGROUND OF THE INVENTION

1. Field of the Invention

The invention relates to a microwave leakage field sensor for measuring moisture and/or density of dielectric materials.

2. Description of the Related Art

Both for application under conditions of a harsh industrial process and for serial measurement in the laboratory, microwave resonator technology affords the possibility of rapidly and precisely acquiring a statement about the moisture and density of the product to be investigated. What is essentially responsible for this is the particular method of separating the influence of moisture and density, which method can be employed with the use of resonators (EP 0 468 023).

In the resonator method, a standing microwave is generated in a suitable metallic cavity. An essential feature of this method consists in not just acquiring the no-loss effects of the interaction between the material moisture and the microwaves, that is to say all the property changes which are dominated by the real part of the dielectric constant. Rather the resonator method also enables the microwave power losses which influence the measurement result to be limited to the attenuation in the product (conversion into heat) and hence corruption due to other losses (leakage losses at surfaces or at coarse-grained scattering centers in the product, radiation losses, etc.) to be avoided. If a moist dielectric material is introduced into the resonator, then the resonant frequency is shifted and the width of the resonant curve increases. Density and moisture can be determined from these changes, as is explained in the abovementioned document.

The method presupposes the use of a resonator which is closed to a greater or lesser extent and from which no microwave energy can escape. Specifically, if field energy is lost by radiation, then this results in a corruption of the line width and of the resonant frequency, so that density and moisture can no longer be determined.

The limits in practical application of cavity resonators are imposed due to the fact that the product to be measured must be put into the sample tube of the applicator. In the case of many products, however, that is only possible in laboratory measurement if laboratory personnel fill the product manually into the sample applicator. In process measurements, in the case of products with good flowing or pouring behavior it is possible for a measurement to be effected in a bypass by transferring product from the main stream with the aid of conveying elements, filling it into the measurement tube and then conveying it back into the main stream again.

It is therefore desirable for process measurement technology to develop, as an expansion, a measuring device which has all the advantages of the patent, mentioned in the introduction, of a density-independent resonator measurement method for measuring moisture and, at the same time, can be directly incorporated in the main stream of the product flow without interfering with the process.

Although there are no difficulties at all in conducting microwaves from waveguides or cavities into the free space, so that the microwaves impinge on large-area plates, a stream of material in an industrial process, etc., in doing so an antenna-like radiation of microwave energy takes place, which, as already mentioned, effects the shifting of the resonant frequency and the widening of the resonant curve and thus corrupts the measurement result.

In the case of a previously known open leakage field resonator, the standing wave is generated by a coaxial line which is open on one side, resonator frequency and quality factor of the resonator being altered by a dielectric in the leakage field (Mesures Regulation Automatisme., Vol. 50, No. 1, January 1985, Paris FR, pages 67–70, XP002057631). The essential deficiency of this arrangement is that this form of leakage field has a distinct radiation behavior perpendicularly to the direction of the coaxial conductor. As a result, the essential precondition is not satisfied in order to be able to utilize the measurement of the losses and ot the resonant frequency shift for the purpose of separating moisture and material density. The layer thickness of the sample, the contact pressure between sensor and sample, the form of the sample, etc thus also have an interfering effect on the measurement signal.

A further previously known sensor with leakage field at the open line end of a coaxial conductor is intended to be used for measuring moisture (Thompson F: "Moisture Measurement Using Microwaves", Measurement and Control, Vol. 22, No. 7, September 1989, pages 210–215, XP000052731). In order to gain a certain degree of control over the problem of radiation and hence of the diverse interfering influences (form of the sample, etc.), the leakage field is limited to "a few millimeters penetration depth into the sample" This also does not allow reliable and accurate measurements for measuring moisture and/or density of samples of relatively large dimensions.

SUMMARY OF THE INVENTION

The object consists in providing a leakage field sensor in the case of which, although the microwave field occurs in the space in front of a certain area, the undesirable antenna-like radiation virtually does not occur.

According to the invention, it was discovered from the inventors' calculations and experiments that this can be achieved by virtue of the fact that the microwave leakage field sensor is of essentially rotationally symmetrical design and transmissive for electromagnetic radiation in the axial direction toward at least one side, and that an essentially rotationally symmetrical alternating field of standing waves can be generated in it, the spatial period of which field in the peripheral direction is less than the vacuum wavelength at the frequency of the alternating field.

In other words, an essentially rotationally symmetrical electromagnetic alternating field in the form of a standing wave is generated, in the case of which the wavelength at the generation location is substantially less than in the free space. The field has a circumference and the distance along the circumference between points of equal field strength is substantially shorter than the wavelength of electromagnetic waves at the frequency of said field in a vacuum. As a result of this difference in the wavelengths at the location where the alternating field is generated and in the free space, the effect according to the invention occurs whereby although the microwaves penetrate a certain distance into the space, the microwave field strength decreases to a very great extent with distance from the leakage field sensor, with the result that virtually no microwave field strength is radiated. This is based essentially on the fact that extinction on account of interference occurs in the far field and only the near field remains.

The invention therefore provides a sensor which may also be of planar design, is designed, on the one hand, as a microwave resonator and is thus accessible to evaluation electronics based on the patent described. On the other hand, an electromagnetic field is generated above a planar sensor surface, which field projects into the product to be measured and has no radiation losses as long as the dielectric constant of the product lies below a critical limit value—which can easily be complied with in the practice of products occurring in an industrial context. Under these conditions, the losses measured by the planar resonator technique arise not as a result of radiation effects but rather as a result of the heat conversion within the product—as in the case of the cavity resonator. The measurement is thus possible from one side of large-area materials, such as, for example, wooden boards, masonry slabs, etc. The measurement is also possible by incorporation in container walls, silos or in the moving product stream within the process installations, etc.

An advantageous embodiment is distinguished by the fact that the leakage field sensor has a metal wire in the form of a closed conductor loop surrounded by a dielectric.

In the case of such conductor loops, it can be difficult to couple in the radiofrequency, in particular microwaves. Another embodiment, in which these problems are avoided, is distinguished by the fact that the leakage field sensor has a circular-cylindrical resonator which is operated in the $E_{m10}$ mode and has a thin, metallic end face interrupted by a central opening and is filled with a dielectric. In this case, m=1,2,3, . . . is the azimuthal mode characteristic number, 1 (=one) is the radial mode characteristic number and 0 (=zero) is the axial mode characteristic number Such a mode has 2 m circle segments in which field lines run alternately from the shortest path from the bottom to the covering plate and vice versa. In the radial direction, the field gradually increases from zero, proceeding from the center of the resonator, exceeds a maximum and becomes zero again at the edge of the resonator. With an increasing mode characteristic number m, the field maximum moves ever further to the wall field region of the resonator. The electric field lines exit from the resonator space through the opening in the end face and merge with the field lines in the opening region of a neighboring circle segment to form a curved field line profile into the space. This field line profile resembles the field line profile of the circular current resonant. As long as no measures are implemented to prevent radiation, the main radiation direction is the radial direction parallel to the end face.

The relative dielectric constant of the dielectric will be chosen differently, depending on the application. It should be at least 2 in one advantageous embodiment, at least 5 in a further embodiment, and at least 10 in an even further embodiment. At the same time, if the dielectric in the case of the conductor loop is comparatively thin, the dielectric constant $\in$ must be chosen such that it is larger than in the case of the dielectric-filled cavity, in order to obtain comparable effects.

In these embodiments, the azimuthal mode characteristic number should advantageously be at least approximately 3, and at least approximately 10 in other advantageous cases.

The aim whereby the electric field has a shorter distance around its circumference between points of equal field strength at the generation location than the wavelength of electromagnetic waves at the frequency of the field in a vacuum can be achieved, in another advantageous embodiment, by virtue of the fact that the leakage field sensor has a metallic conductor shaped like a rosette, the oscillations being formed maximally either on the outside on each (or each second, each third, etc.) curve or correspondingly on the inside By choosing the frequency of the signal fed in such that a maximum and a minimum field strength are respectively alternately formed on the outer arc or on the inner arc of the rosette (if there is dependence on the coupling chosen) and form a standing wave along the circle, the number of wavelengths on the metallic structure is equivalent to the mode characteristic number m of the circular-cylindrical cavity resonator. At a suitable distance, the field structure is thus equivalent to that of the circular-cylindrical resonator mentioned.

This effect can be further reinforced by arranging the conductor on a dielectric substrate or in such a dielectric substrate, where the abovementioned effect of the rosette-like current profile, which like-wise signifies a shortening of the distance around its circumference between points of equal field strength at the generation location, is reinforced by the wavelength-shortening effect of the dielectric.

The distance along the circumference of the field between points of equal field strength is advantageously at least approximately 1.5 times, even more advantageously at least approximately 2.5 times, and in other advantageous embodiments at least approximately 3.5 times, less than the wavelength of electromagnetic waves at the frequency of the field in a vacuum.

The leakage field sensor according to the invention can be used in a wide range of frequencies, its dimensions and, if appropriate, the dielectric constant having to be adapted to the frequency, of course. The leakage field sensor according to the invention can easily be used in a range from 0.1 GHz to above 20 GHz.

BRIEF DESCRIPTION OF THE DRAWINGS

The invention is described by way of example below using advantageous embodiments with reference to the appended drawings, in which.

DESCRIPTION OF THE PREFERRED EMBODIMENT

Figure 1:
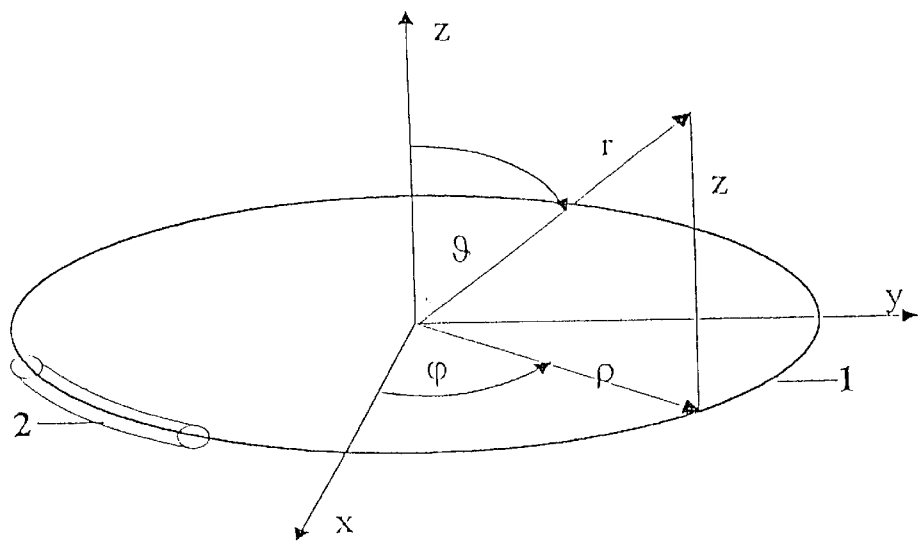
FIG. 1 shows a diagrammatic illustration of a conductor loop in the form of a wire.
Figure 2:
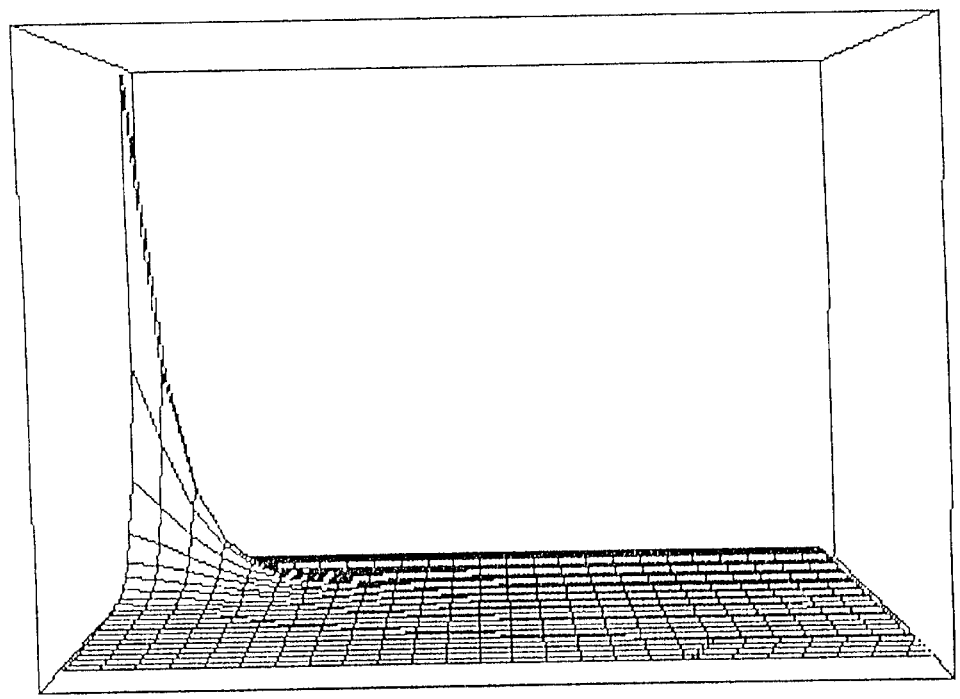
FIG. 2 shows the microwave field strength as a function of the location in the leakage field sensor of FIG. 1.

FIG. 1 shows a wire loop 1 in which a standing electromagnetic wave can be generated The wire loop 1 is surrounded by a thin dielectric, which is indicated at 2. On account of this dielectric, the wavelength in the current loop 1 has a smaller value than in the free space. The resulting microwave field strength for this arrangement is evident in FIG. 2. The intensity is plotted upward, the z-axis toward the right and the radial axis (x or y) toward the front. As can be seen, the microwave field strength decreases very rapidly with an increasing distance z from the wire loop 1 within the dimensions of a wavelength. Therefore, no appreciable radiation takes place.

The results of calculations of the inventors are listed in Table 1. The critical values of the dielectric constant $\in$ for the different mode characteristic numbers for which the radiated power is reduced below the value of 0.01% of the radiation of the bare metallic circular conductor are entered in each case in said table. The radius of the conductor loop which is to be chosen for the realization of a resonant frequency of 2.5 GHz given the relevant mode and the critical value of the dielectric constant is specified in the last column m, the mode characteristic number, is in this case the number of half-waves on the circular conductor 1 of FIG. 1.

| Mode characteristic number m | Effective dielectric constant ε so that radiation <0.01% | Shortening factor with respect to vacuum wavelength (√ε) | Maximum circle radius for f = 2.5 GHz |
| --- | --- | --- | --- |
| 1 | 15625 | 125 | 0.15 mm |
| 2 | 141.7 | 11.9 | 3.2 mm |
| 3 | 31.9 | 5.65 | 10.1 mm |
| 4 | 15.0 | 3.87 | 19.7 mm |
| 5 | 9.5 | 3.08 | 31.0 mm |
| 6 | 7.0 | 2.65 | 43.3 mm |
| 7 | 5.6 | 2.37 | 56.5 mm |
| 8 | 4.7 | 2.17 | 70.5 mm |
| 9 | 4.1 | 2.02 | 84.9 mm |
| 10 | 3.7 | 1.92 | 99.3 mm |

Figure 3:
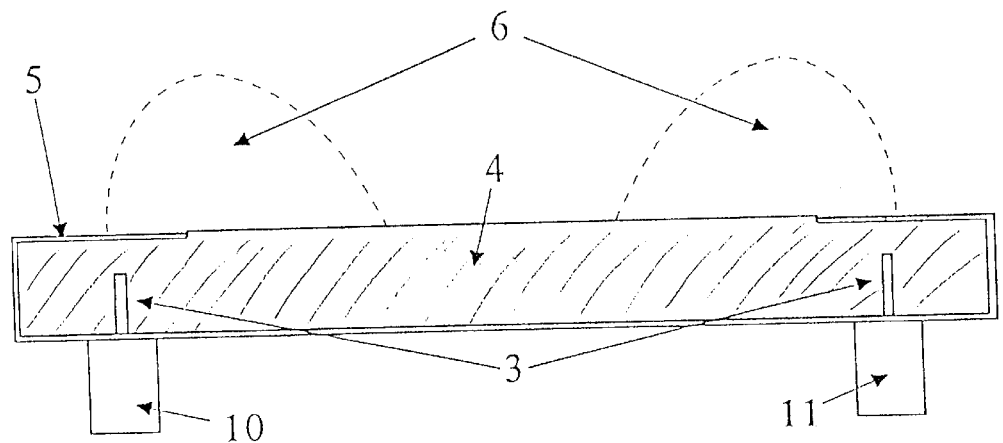
FIG. 3 shows a cross section through a second embodiment of the leakage field sensor according to the invention.

FIG. 3 shows a different embodiment of the leakage field sensor according to the invention. In this case, the input coupling and output coupling 11 of the microwaves take place via coaxial lines and capacitively effective coupling pins 3, which are fitted symmetrically with respect to the center of the resonator at a distance K such that they are situated, on the one hand, under the metallic cover of the covering layer and, on the other hand, in the vicinity of the maximum of the electrical resonant field. The actual resonator is formed by the circular dielectric ceramic body 4 with dielectric constant ∈, diameter D, layer thickness s, and a thin (that is to say situated with a layer thickness of less than 0.1 mm) metalization layer which bounds the ceramic body everywhere except for the concentrically made opening in the metalization layer in the resonator covering layer (diameter O). Above this the actual measurement zone is made, with the sketched leakage field regions 6.

An example of practical implementation is a sensor in the operating range up to 4 GHz, with which the resonant modes $E_{410}$, $E_{510}$, $E_{610}$, $E_{710}$, $E_{810}$ and $E_{910}$ can be excited in a single design In this case, D=145 mm, O=90 mm to 120 mm (depending on the size of the desired leakage field), s=3.2 mm, ∈=9.2.

Technically, it is possible to realize planar sensors up to ceramic fillings of ∈=100. For higher values of the dielectric constant, field minima and maxima already lie so close together that the antenna couplings already generate excessively great inhomogeneities in the resonator space.

Figure 4:
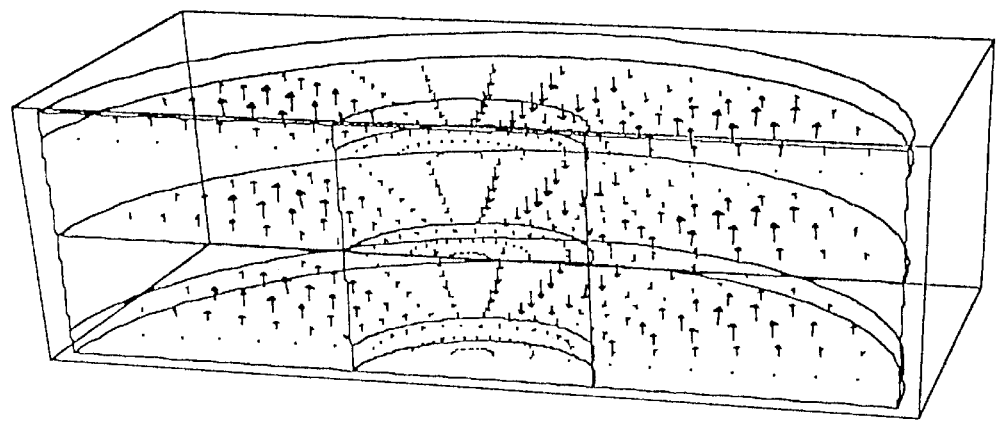
FIG. 4 shows the profile of the microwave field lines in the leakage field sensor of FIG. 3.

FIG. 4 shows the field line profile $E_{310}$ resonant mode of a corresponding closed circular-cylindrical resonator. Through the opening in the upper end face, it is then possible to generate a field pattern as in the case of the first embodiment of the annular conductor with m=3.

Figure 5:
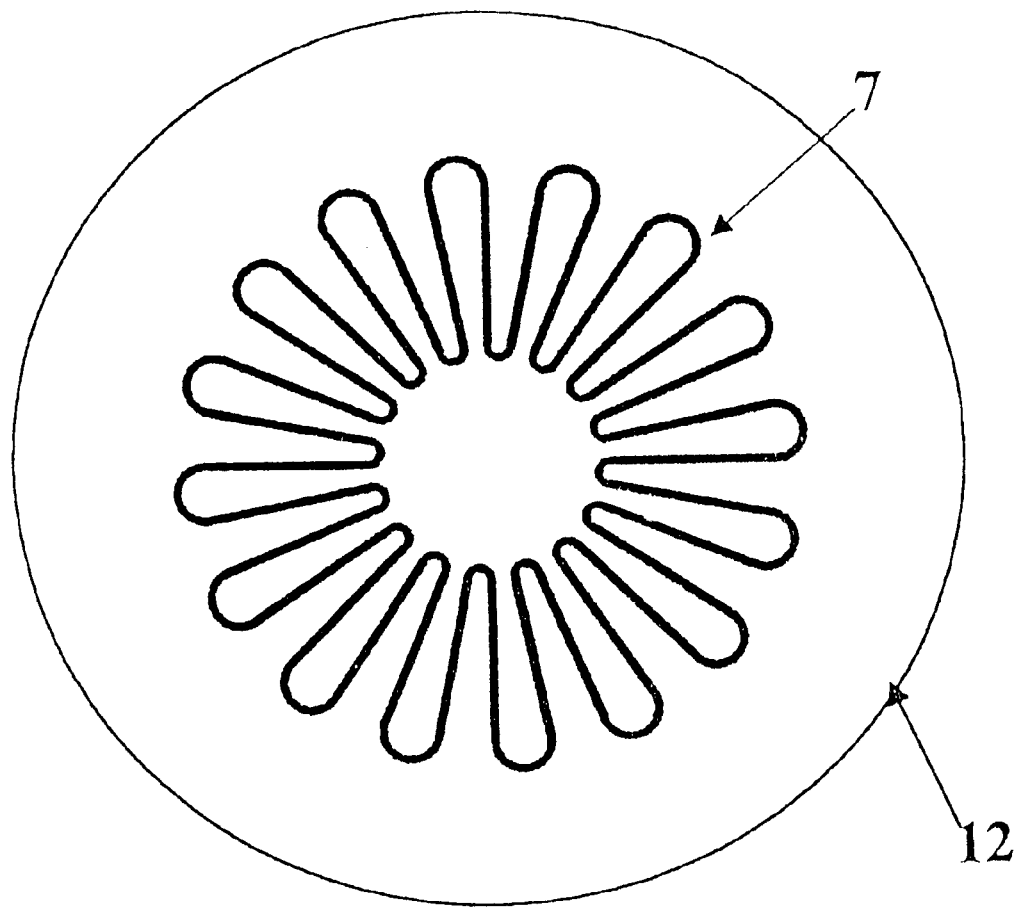
FIG. 5 shows a third embodiment of the leakage field sensor according to the invention.

A third embodiment is shown in FIG. 5. The metallic line 7 forms a rosette structure situated on or in a substrate, in particular a dielectric substrate, which is indicated at 12. The line is in this case wound in a meander-like manner in one plane and about a circle. An electromagnetic wave is coupled in by means of suitable input coupling in the form of coupling pins or coupling lines which are situated either on the underside of the substrate or on the top side laterally with respect to the rosette structure at a sufficient distance from one another. This wave is guided along the metallic line. Resonance is formed in such a way that the oscillation maxima are formed either on the outside in each (or each second, each third, etc.) curve or correspondingly on the inside By choosing the frequency of the signal fed in such that a maximum and a minimum field strength are respectively alternately formed on the outer arc or on the inner arc of the rosette (in dependence on the coupling chosen) and form a standing wave along the circle, the number of wavelengths on the metallic structure is equivalent to the mode characteristic number m At a suitable distance, the field structure is thus equivalent to that of the circular resonator.

The shortening of the distance between points of equal field strength along the inner or outer circumference of the field (important for avoiding radiation) in the circular arrangement results from the additional distance which the wave has to cover by virtue of the turns along the metallic conductor.

By a suitable selection of the number of turns of the rosette and also of the diameter of the inner and outer circles, the shortening of the distance between points of equal field strength along the inner or outer circumference of the field can be varied within wide ranges and the critical values for freedom from radiation for the shortening factor can comfortably be exceeded.

A further possible configuration is afforded by the selection of a suitable substrate having a correspondingly high dielectric constant. A typical exemplary embodiment of a radiation-free structure for the resonant frequency of approximately 2.5 GHz is given by the following quantities of the outer diameter A, inner diameter B, number of turns of the rosette N, layer thickness d of the substrate and dielectric constant ∈ thereof, which in each of the cases fulfills the criteria of freedom from radiation (for example a wavelength shortening factor of 12 in the case of the mode characteristic number m=16 results for the first example in the table).

| A | B | N | d | ε |
| --- | --- | --- | --- | --- |
| 50 mm | 6 mm | 32 | 1.5 mm | 3.1 |
| 47 mm | 7 mm | 16 | 1.5 mm | 2.2 |
| 76 mm | 42 mm | 16 | 1.5 mm | 3.1 |
| 52 mm | 20 mm | 8 | 1.5 mm | 3.1 |

What is claimed is:
1. A microwave leakage field sensor for measuring moisture and density of dielectric materials, said microwave leakage field sensor comprising:
a resonator body having a substantially planar sensor surface and constructed of a dielectric material having a relative dielectric constant $\in_1$, said resonator body surrounded by a metallic layer except for a rotationally symmetrical opening on said sensor surface, said opening having a circumference and a diameter O, so that said resonator body is transmissive for electromagnetic radiation toward said sensor surface;
input coupling means for coupling electromagnetic energy into said resonator body to produce a substantially rotationally symmetrical field of standing electromagnetic waves in the resonator body, said field having an energy, a near leakage field adjacent said sensor surface that repeats m times around said circumference, where m is an integer and a far leakage field extending axially beyond said near leakage field; and
output coupling means for coupling said field to sensing means for sensing changes in a resonant frequency and a Q factor of said field,
wherein said relative dielectric constant $\in_1$, said diameter O and an operational frequency are selected such that a ratio of a wavelength of electromagnetic waves at the operational frequency of said field in a vacuum to a distance along said circumference between points of equal field strength of the near leakage field is at least 1.5, producing extinction of the far field by destructive interference, resulting in a sensor in which substantially all change in the resonant frequency and Q factor of the field are attributable to the dielectric constant $\epsilon_2$ and dielectric loss, respectively, of a test dielectric material placed in said near leakage field.

2. The microwave leakage field sensor of claim 1, wherein less than 0.01% of the energy of the field of standing electromagnetic waves in the resonator body is radiated away from the sensor.

3. The microwave leakage field sensor of claim 1, wherein said ratio has a range of 1.5 to 3.5.

4. The microwave leakage field sensor of claim 1, wherein said ratio has a range of 1.5 to 3.5.

5. The microwave leakage field sensor of claim 1, wherein said leakage field repeats 1 time in a radial direction across said sensor surface and does not repeat in the axial direction due to said destructive interference.

6. The microwave leakage field sensor of claim 1, wherein m is at least 3.

7. The microwave leakage field sensor of claim 6, wherein m is between 3 and 10.

8. A microwave leakage field sensor for measuring moisture and density of dielectric materials, said microwave leakage field sensor comprising:

a continuous metallic conductor disposed on a sensor surface of a dielectric substrate, the opposite side of the dielectric substrate being covered with a metallic layer, said conductor having a length, with the conductor arranged to meander back and forth between inner and outer circumferences to form a rotationally symmetrical pattern;

input coupling means for coupling electromagnetic energy to said conductor to produce a standing electromagnetic wave on said conductor at a resonant frequency f, said wave repeating m times along the length of said conductor to form a rotationally symmetrical field of standing waves having a leakage field projecting axially away from said sensor surface, where m is an integer, said leakage field having maxima and minima and said resonant frequency f is selected so that field maxima and minima are alternately formed adjacent either said inner or outer circumference; and output coupling means for coupling said field to sensing means for sensing changes in a resonant frequency and a Q factor of said field, wherein a ratio of a wavelength of electromagnetic waves at the frequency of said field in a vacuum to a distance along said inner or outer circumference between points of equal field strength in said leakage field is at least 1.5, producing extinction of the leakage field by destructive interference, resulting in a sensor in which substantially all change in the resonant frequency and Q factor of the field of standing waves are attributable to the dielectric constant and dielectric loss of a test dielectric material passing through said field.

9. The microwave leakage field sensor of claim 8, wherein said conductor is arranged in said dielectric substrate.

10. The microwave leakage field sensor of claim 8, wherein said ratio has a range of 1.5 to 3.5.

11. The microwave leakage field sensor of claim 8, wherein said leakage field does not repeat in the axial direction due to said destructive interference.

12. The microwave leakage field sensor of claim 8, wherein said field has an energy and less than 0.01% of said energy is radiated from said sensor.

13. A method for measuring the moisture and density of dielectric materials using a substantially radiation free microwave leakage field sensor, comprising the steps of:

generating a rotationally symmetrical field of standing electromagnetic waves in said sensor, said field having a corresponding leakage field projecting axially away from a sensor surface, said leakage field having a circumference and in which a ratio of a wavelength of an electromagnetic wave at the frequency of said field in a vacuum to a distance along said circumference between points of equal field strength is at least 1.5;

causing a dielectric material to pass through said leakage field;

sensing shifts in a resonant frequency and a Q factor of said field caused by a dielectric constant and a dielectric loss, respectively, of said dielectric material, wherein said leakage field does not repeat in the axial direction due to destructive interference and substantially all change in the resonant frequency and Q factor of said field are attributable to the dielectric constant and dielectric loss of said dielectric material.

14. A microwave leakage field sensor comprising:

a resonator body having a planar sensor surface and constructed of a dielectric material having a relative dielectric constant $\epsilon_1$, said resonator body surrounded by a metallic layer except for a rotationally symmetrical opening in said metallic layer on said sensor surface so that said sensor is transmissive for electromagnetic radiation through said opening;

input coupling means for coupling electromagnetic energy into said resonator body to produce a substantially rotationally symmetrical field of standing electromagnetic waves in said resonator body at a selected operational frequency, said field having a near leakage field adjacent said sensor surface and a far leakage field extending axially beyond said near leakage field; and output coupling means for coupling said field to sensing means for sensing changes in a resonant frequency and a Q factor of said field, wherein said relative dielectric constant $\epsilon_1$, said diameter O and said operational frequency are selected such that said far leakage field is extinguished by destructive interference, resulting in a microwave leakage field sensor in which substantially all change in the resonant frequency and Q factor of said field of standing electromagnetic waves are attributable to a dielectric constant $\epsilon_2$ and dielectric loss, respectively of a test dielectric material in said near leakage field.

15. The microwave leakage field sensor of claim 14, wherein said resonator body is a circular cylindrical resonator.

16. The microwave leakage field sensor of claim 15, wherein a ratio of the wavelength of electromagnetic waves at said operational frequency in a vacuum to a distance between points of equal field strength in said near leakage field is at least 1.5.

17. The microwave leakage field sensor of claim 16, wherein said ratio has a range of 1.5 to 3.5.

* * * * *

UNITED STATES PATENT AND TRADEMARK OFFICE
CERTIFICATE OF CORRECTION

PATENT NO. : 6,316,946 B2
DATED : November 13, 2001
INVENTOR(S) : Herrmann et al.

It is certified that error appears in the above-identified patent and that said Letters Patent is hereby corrected as shown below:

<u>Column 7,</u>
Line 50, after "extinction of" delete "the" and insert -- a far --.

Signed and Sealed this

Fifteenth Day of October, 2002

Attest:

Attesting Officer

JAMES E. ROGAN
*Director of the United States Patent and Trademark Office*